United States Patent
Zacche' et al.

(10) Patent No.: US 8,877,941 B2
(45) Date of Patent: Nov. 4, 2014

(54) PROCESS FOR THE RESOLUTION OF MEDETOMIDINE AND RECOVERY OF THE UNWANTED ENANTIOMER

(71) Applicants: Matteo Zacche', Vanzago (IT); Fulvio Gerli, Paderno Dugnano (IT); Pier Andrea Gatti, San Genesio Ed Uniti (IT)

(72) Inventors: Matteo Zacche', Vanzago (IT); Fulvio Gerli, Paderno Dugnano (IT); Pier Andrea Gatti, San Genesio Ed Uniti (IT)

(73) Assignee: Edmond Pharma S.r.l., Paderno Dugnano (IT)

( * ) Notice: Subject to any disclaimer, the term of this patent is extended or adjusted under 35 U.S.C. 154(b) by 0 days.

(21) Appl. No.: 13/777,003

(22) Filed: Feb. 26, 2013

(65) Prior Publication Data

US 2013/0225832 A1 Aug. 29, 2013

(30) Foreign Application Priority Data

Feb. 29, 2012 (IT) .............. MI2012A0311

(51) Int. Cl.
*C07D 233/58* (2006.01)
*C07D 233/64* (2006.01)

(52) U.S. Cl.
CPC ............ *C07D 233/58* (2013.01); *C07D 233/64* (2013.01)
USPC ....................................... 548/346.1

(58) Field of Classification Search
CPC ..................................... C07D 233/64
USPC ..................................... 548/346.1
See application file for complete search history.

(56) References Cited

U.S. PATENT DOCUMENTS 4,910,214 A * 3/1990 Karjalainen et al. .......... 514/396

OTHER PUBLICATIONS

Cordi et al. Synth. Commun. 1996, 26(8), 1585-1593.*
Escoubet et al. Eur. J. Org. Chem. 2006, 14, 3242-3250.*

* cited by examiner

*Primary Examiner* — Samantha Shterengarts
*Assistant Examiner* — Amanda L Aguirre
(74) *Attorney, Agent, or Firm* — Silvia Salvadori, P.C.

(57) ABSTRACT

A new and efficient process to obtain Medetomidine enantiomers, a selective and potent α2-receptor agonist, is presented. Such process comprises a resolution step and a racemization reaction, to be able to recover the unwanted enantiomer which can be recycled as starting material.

6 Claims, No Drawings

PROCESS FOR THE RESOLUTION OF MEDETOMIDINE AND RECOVERY OF THE UNWANTED ENANTIOMER

This non-provisional application claims priority to and the benefit of Italian Application No. MI2012A000311 filed on Feb. 29, 2012, the content of which is incorporated herein by reference in its entirety.

The present invention relates to a process for the resolution of Medetomidine enantiomers.

BACKGROUND AND PRIOR ART

Medetomidine of formula 1

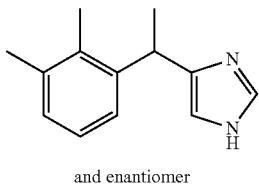

and enantiomer is a potent, selective α2-receptor agonist, used as an antihypertensive agent and as a sedative and analgesic for veterinary and human use.

EP 300 652 discloses that the S-enantiomer of Medetomidine, namely Dex-Medetomidine, possesses an enhanced α2-selectivity and potency when compared with the racemic mixture.

EP 300 652 also discloses a resolution method to separate the racemic Medetomidine in its single enantiomers. According to EP 300 652, the racemate is converted into a mixture of diastereoisomer salts which are then separated by repeated crystallisations.

The separation of the enantiomers is illustrated in an example, in which after several repeated crystallisations, a total yield of less than 30% is obtained.

Considering that such a process is time consuming and hence not suitable for an efficient industrial application, it would be desirable to find a more practical and efficient process to produce the target enantiomers with high optical purity and in high yield.

DESCRIPTION OF THE INVENTION

It has now been found that Medetomidine base enantiomers undergo selective salification when treated with a determinate amount of a selected enantiomerically pure carboxylic acid, leading to the separation of the target enantiomer as a salt, while leaving the unwanted one in solution as free base.

Moreover, the unwanted enantiomer which is left in solution as a free base, can be racemized back and converted into a mixture of the two enantiomers, making it possible to recycle it as starting material, thereby surprisingly increasing the final yield of the process.

More particularly, the present invention relates to an improved process for preparing Medetomidine S- and R-enantiomers respectively of formula 2 and 3

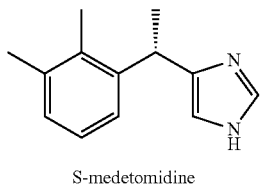

S-medetomidine

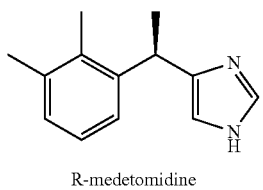

R-medetomidine which process comprises a resolution step to separate the desired enantiomer, and a racemisation step to recycle the unwanted one.

The resolution step according to the invention is carried out by selective salification instead of fractional crystallisation. In fact, it has been found that using only half mole of acid per mole of Medetomidine, a selective salification can be performed, thus leading to the crystallisation of the desired enantiomer in the form of a salt, while the undesired enantiomer remains in solution in the form of free base.

A selective salification is much more efficient than a fractional crystallisation, and is also a very different chemical-physical process. In fact, in the case of a fractional crystallisation all the product is salified with an acid, and thus two diastereomeric salts are formed. A portion of one of the two salts then crystallizes, thus establishing an equilibrium with loss of yield and enantiomeric purity, because the solubility of the two diastereomeric salts is very much similar.

Conversely, in the case of a selective salification, only the desired enantiomer is salified and thus only the corresponding diastereomeric salt precipitates. In this conditions the solubility of the free base of the undesired enantiomer, which is left in the solution, is so much higher than the solubility of the salt of the desired enantiomer, that the establishing of an equilibrium is not possible. The salt obtained by selective salification with an enantiomerically pure carboxylic acid, which is preferably selected from the group comprising but not limited to malic acid, camphorsulphonic acid, tartaric acid, dibenzoyltartaric acid, ditoluyltartaric acid, pivaloyltartaric acid, has solubility lower than 5 g/L, leading to an increase in the process yield.

Furthermore, in this way a very stable crystallisation system can be obtained, thus making it possible to selectively separate the salt of the desired enantiomer from the reaction medium. This is accomplished by using the correct amount of acid in order to achieve a selective salification of only one enantiomer.

The crystallisation system obtained is stable for a prolonged time (more than 24 hours), thus allowing an industrial production much more superior to any method based on fractional crystallisation.

This method is advantageous over the methods known in the prior art in terms of industrial procedure, and makes possible to obtain the enantiomers of Medetomidine with high optical purity in high yields.

Accordingly to the present invention, the compound of formula 1 is efficiently resolved in an alcoholic solvent, selected from the group (but not limited to) of straight C alcohols such as ethanol, methanol and the like, being them anhydrous or with variable contents of water, using 0.5 moles of an enantiomerically pure dicarboxylic acid per mole of racemic Medetomidine.

The yield of the improved process according to the invention is higher than 65%, which is more than twice the yield of the methods known in the art. The enantiomeric purity obtained is higher than 99%.

In yet another aspect, the unwanted enantiomer can be recycled as starting material with a racemisation step. In this way the efficiency of the process can be increased, making it more economical and efficient.

The racemisation is effected by treating the mother liquors from the resolution process, containing the unwanted enantiomer as free base, with a radical initiator, such as (but not limited to) dibenzoyl peroxide or azobisisobutyronitrile, optionally in the presence of light as activator. The racemic material is then isolated and purified with methods know in the art.

In this way the overall yield of the process can be greatly increased.

In greater detail, the process presented comprises the following steps:
a) preparing a solution of Medetomidine base in a suitable solvent or solvent mixture thereof;
b) adding the solution with half mole of an enantiomerically pure carboxylic acid;
c) optionally heating the solution and then cooling it until complete precipitation of the desired salt;
d) purifying the desired salt by treating it with a suitable solvent, optionally under heating;
e) isolating the desired salt and converting it to the free base with methods known in the art;
and optionally
f) treating the mother liquors from step c) with a radical initiator, optionally in the presence of light as activator, to racemise the unwanted enantiomer;
g) isolating the racemic material with methods known in the art and recycling it to step a).

In summary, the present invention discloses an economical, efficient and less time consuming process for the manufacture of enantiomerically pure enantiomers of Medetomidine.

EXAMPLE 1 (RESOLUTION)

Racemic Medetomidine base (200 g, 1 mol), acetone (1100 mL) and ethanol (70 mL) are charged in a reactor and L-(+)-malic acid (67 g, 0.5 mol) is added in one portion. The mixture is then heated to reflux until complete dissolution is obtained. The solution is then gradually cooled to about 20° C., and the resulting slurry is then filtered washing with acetone. The solid thus obtained (125 g) is charged again in the reactor with ethanol (500 mL) and the slurry is heated to reflux for half an hour. After cooling and filtering, about 110 g of dry weight of the malate salt is obtained (0.328 mol, i.e. 66% of theoretical yield).

The crystalline product is neutralized with dilute sodium hydroxide at pH>12 and extracted with methylene chloride. The phases are separated and the organic phase is concentrated to dryness to obtain about 65 g of (S)-Medetomidine with an enantiomeric purity of 99.9% (HPLC analysis on chiral stationary phase).

EXAMPLE 2 (RACEMISATION)

The acetone/ethanol mother liquors from the resolution step are evaporated to dryness, treated with dilute sodium hydroxide until pH 14 and extracted with methylene chloride. The organic phase is separated and concentrated to dryness obtaining a mixture of enantiomers enriched at 75% with the unwanted enantiomer. About 3 grams of this mixture is dissolved in methanol (50 mL), and dibenzoyl peroxide (7 g) is added. The solution is put under the light from an incandescent bulb for about 3 hours, under stirring, then it is concentrated to dryness and partitioned between methylene chloride and dilute sodium hydroxide. The organic phase is separated, diluted with the same volume of methanol and brought to pH 1 with hydrochloric acid, then it is concentrated to dryness and triturated with acetone. About 1 gram of racemic Medetomidine hydrochloride is thus obtained.

The invention claimed is:

1. A process for a resolution of Medetomidine enantiomers comprising:
a) preparing a solution of Medetomidine base in a suitable solvent or solvent mixture;
b) combining the solution with of half a molar equivalent of an enantiomerically pure carboxylic acid;
c) optionally heating the solution and then cooling it until complete precipitation of a desired enantiomer as a salt;
d) purifying the desired salt by treatment with a suitable solvent, optionally under heating;
e) isolating the desired salt and converting it to the free base,
and further recycling the undesired enantiomer with the following steps:
f) treating a mother liquor from step c) with a radical initiator, optionally in the presence of light as activator; and
g) isolating a racemic material and recycling it to step a).

2. A process according to claim 1 wherein the desired enantiomer is the S-enantiomer.

3. A process according to claim 1 wherein the enantiomerically pure acid is selected from malic acid, camphorsulfonic acid, tartaric acid, dibenzoyltartaric acid, ditoluyltartaric acid and pivaloyltartaric acid.

4. A process according to claim 3 wherein the acid is (+)-malic acid.

5. A process according to claim 1 wherein the solvent of step a) is a straight alcohol.

6. A process according to claim 5 wherein the alcohol is dry or hydrate methanol or ethanol.

\* \* \* \* \*